United States Patent [19]

Draenert

[11] Patent Number: 5,788,702
[45] Date of Patent: Aug. 4, 1998

[54] APPLICATOR SYSTEM

[76] Inventor: Klaus Draenert, Gabriel-Max-Str. 3, 81545 München, Germany

[21] Appl. No.: 924,250

[22] Filed: Sep. 5, 1997

Related U.S. Application Data

[63] Continuation of Ser. No. 613,531, Mar. 11, 1996, abandoned, which is a continuation of Ser. No. 360,716, filed as PCT/EP93/01510, Jun. 15, 1993, published as WO93/25162, Dec. 23, 1993, abandoned.

[30] Foreign Application Priority Data

Jun. 15, 1992 [DE] Germany .................. 42 19 563.2

[51] Int. Cl.⁶ .................................................. A61B 17/58
[52] U.S. Cl. ........................... 606/92; 606/93; 606/94; 606/95; 604/247; 222/527
[58] Field of Search ............................. 606/92, 93, 94, 606/95; 604/247; 222/527

[56] References Cited

U.S. PATENT DOCUMENTS

| | | | |
|---|---|---|---|
| 3,402,741 | 9/1968 | Yurdin | 222/527 |
| 4,232,670 | 11/1980 | Richter et al. | 128/224 |
| 4,338,925 | 7/1982 | Miller . | |
| 4,405,249 | 9/1983 | Scales | 606/93 |
| 4,546,767 | 10/1985 | Smith | 606/93 |
| 4,625,722 | 12/1986 | Murray | 606/94 |

FOREIGN PATENT DOCUMENTS

| | | |
|---|---|---|
| A-0006430 | 1/1980 | European Pat. Off. . |
| A-0108584 | 5/1984 | European Pat. Off. . |
| A-2656521 | 7/1991 | European Pat. Off. . |
| A-4022985 | 1/1992 | Germany . |
| A-4022986 | 1/1992 | Germany . |
| A-639549 | 11/1983 | Switzerland . |

*Primary Examiner*—Michael Buiz
*Assistant Examiner*—Daphna Shai
*Attorney, Agent, or Firm*—Kinney & Lange, P.A.

[57] ABSTRACT

The invention relates to a one-piece or multipiece application system for applying plastic masses out of a receptacle. The application system (10) comprises a funnel-shaped outlet piece (16) adapted to the receptacle and an elongate application part (30), wherein along the inner surfaces of all parts of the application system no shoulder is formed which could impair the application of the plastic mass.

14 Claims, 2 Drawing Sheets

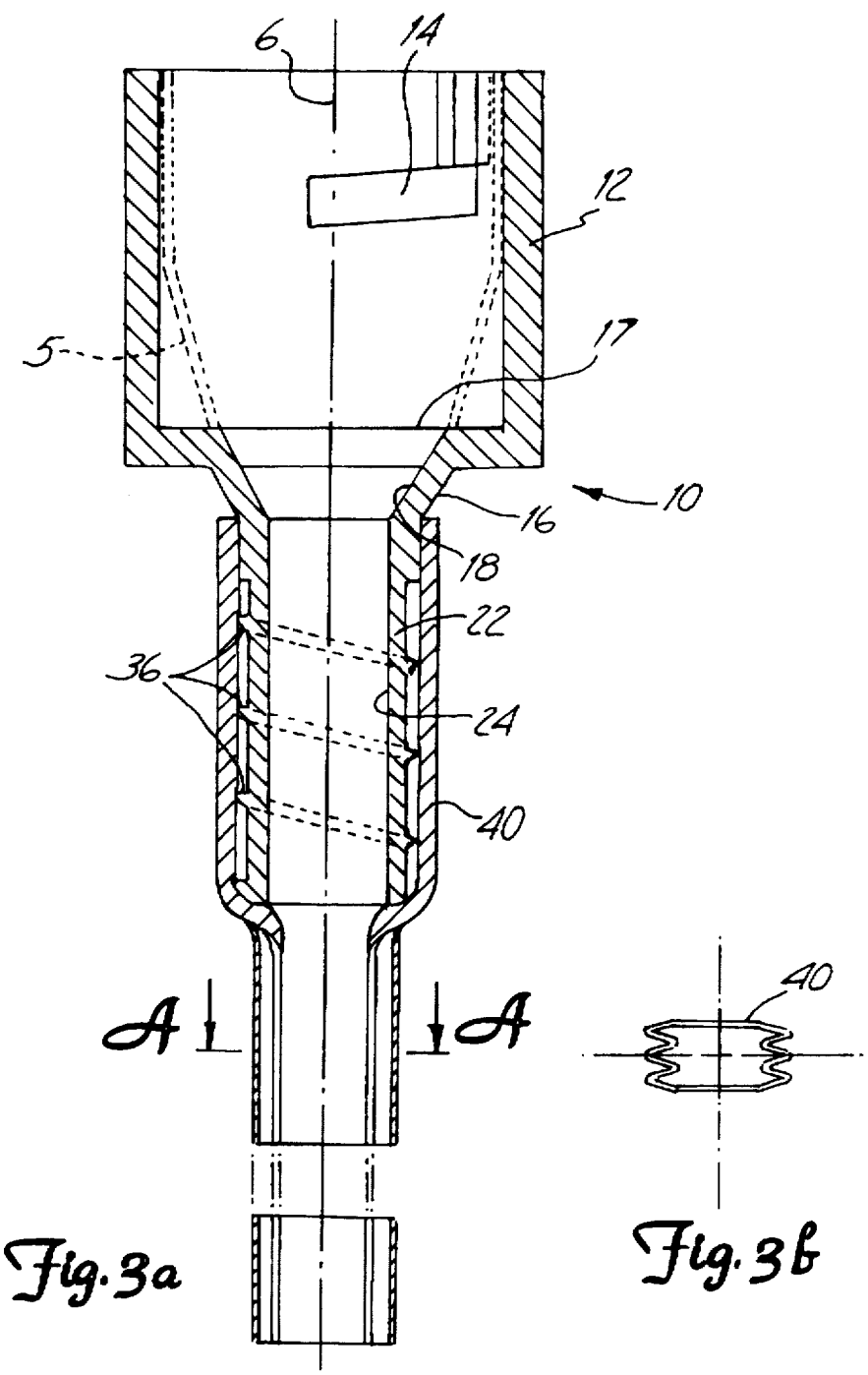

APPLICATOR SYSTEM

This is a continuation of application Ser. No. 08/613,531, filed Mar. 11, 1996 now abandoned; which is a continuation of Ser. No. 08/360,716, filed Dec. 13, 1994; now abandoned, which is a 371 of PCT/EP93/01510, filed Jun. 15, 1993 published as WO93/25162 Dec. 23, 1993.

The invention relates to a one-piece or multipiece application system for plastic masses, for instance plastic organic plastics, such as PMMA bone cements, or inorganic cement masses, as well as the use of the application system, in particular for applying bone cement into a medullary cavity.

As described, for instance, in EP-A-0 170 120 and EP-A-0 262 185, bone cement is applied into the medullary cavity by means of a pistol or syringe out of a preferably cylindrical receptacle having a preferably transverse outlet. In this connection, care should be taken that the bone cement can be applied into the medullary cavity without any substantial losses and fills the medullary cavity completely. Similar requirements must also be met when applying other plastic masses into spaces to be filled. This is, for instance, of particular importance if it must be guaranteed on account of exact dosage instructions that the previously measured plastic mass is completely supplied into the space to be filled.

Thus, it is an object of the invention to provide a device by means of which a plastic mass can be introduced into a space to be filled without any losses out of a receptacle and fills the space as completely as possible.

This object is achieved by the application system according to the invention.

The invention is based on the principle of providing an application system comprising an outlet piece which can be connected with the receptacle and is preferably provided with a funnel-shaped part, and an elongate application part, wherein along the inner surfaces the transitions between the receptacle and the outlet piece as well as between the outlet piece and the application part are flush or even and no shoulder is present which could impair the flow of the plastic mass.

The application system according to the invention can have both a one-piece and a multipiece structure, in particular a two-piece structure. The application system can, for instance, be a one-piece or multipiece cap which can be placed onto the receptacle, for instance on a bone cement cartridge. The cap or the outlet piece and the application part can either be integral or consist of several parts that can be connected with each other.

If the receptacle for the plastic mass is cylindrical, the outlet piece of the application system is preferably funnel-shaped without forming a shoulder relative to the receptacle along their inner surfaces. The funnel-shaped outlet piece forms a transition to the application part without forming any shoulder along the inner surfaces, which application part has preferably a length of about 3 to 25 cm, more preferably about 5 to 20 cm and can, for instance, be a rigid pipe, a tube or snorkel.

It is particularly preferred that the application system is a one-piece or multipiece cap which can be placed onto the outlet of the receptacle, for instance by means of a bayonet catch or a screw thread, such that the inner surfaces of the receptacle and the cap pass into one another without forming any shoulder. The adjustment of the relative position of the cap, such as its rotational position, relative to the receptacle is preferably reproducible, for instance by means of a stop of the bayonet or an exact adaptation of the screwed thread so that the cap is always placed onto the receptacle in the same position. This is particularly advantageous if the outlet of the receptacle is not rotationally symmetrical but, for instance, transverse or elongate. In this case, the inner circumference of the cap at the transition to the receptacle must also be shaped correspondingly and have an elongate cross-section. The reproducible positioning guarantees also in the case of such a rotationally non-symmetrical structure that there is no shoulder at the transition along the inner surfaces of the receptacle and the cap.

The application system preferably consists of two parts and comprises in addition to a main part (cap) that can be connected with the receptacle a fitted tube which is mounted such that the inner diameter of the tube in its non-expanded condition is identical to the inner diameter of the outlet of the cap. The tube may preferably consist of Teflon. The tube mounted on the main part or the cap is preferably held at the main part or the outlet piece of the cap by means of at least one sharp-edged ring profile having an undercut and is thus prevented from sliding back. It can, however, also be fixed to the main part or the cap by means of a thread or a device for receiving a tube clamp or by other fixing means and thus be secured against slipping off.

The elongate application part is preferably foldable, for instance a tube or snorkel that can be folded in a star-like or any other manner. Such a tube or snorkel can easily be introduced in its folded condition into the space to be filled, for instance the medullary cavity, and unfolds by means of the plastic mass introduced into it during the application. At the end of the application, the snorkel or tube filled with the plastic mass completely fills the space to be filled and can subsequently be retracted and removed from the space to be filled, the plastic mass remaining in said space. The introduction of the foldable application part into the space to be filled is facilitated if the free end of the application part can be more easily unfolded than its other end which is connected with the outlet piece or the main part of the cap.

By means of the elongate application part, bone cement, for instance, can be distally applied into the bony bed during the implantation of a hip joint endoprosthesis.

As material for the application system, preferably a sterilizable plastics material, e.g. TPX, a rubber or silicone, polycarbonate or a material having similar properties, a metal or glass is used. It is particularly preferred to use a smooth elastic material or a composite material for the snorkel, which material can develop the function of an air chamber or accumulator, i.e. becomes deformed and expands by means of the mass to be applied, and advances and pushes forward the mass in the snorkel during its subsequent contraction.

The invention will be explained in more detail in the following by means of the drawing, in which:

FIGS. 3a and 3b show a further embodiment of the application system according to the invention.

Figure 1:
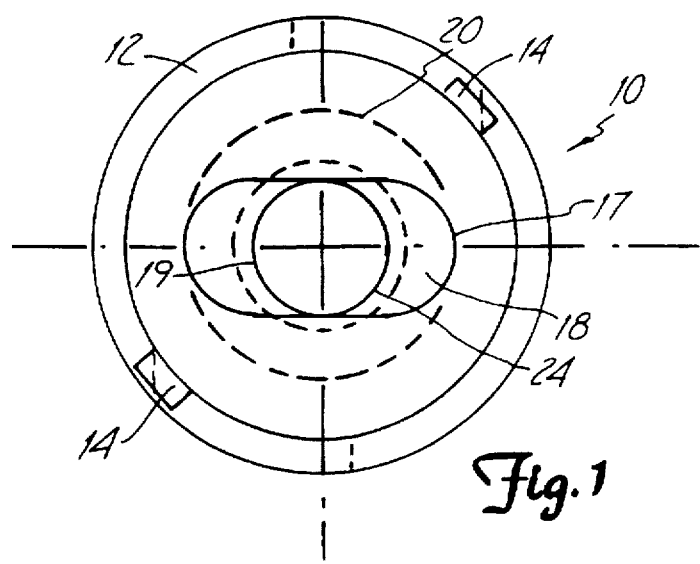
FIG. 1 shows a top view of the application system according to the invention from the direction of the receptacle.
Figure 2:
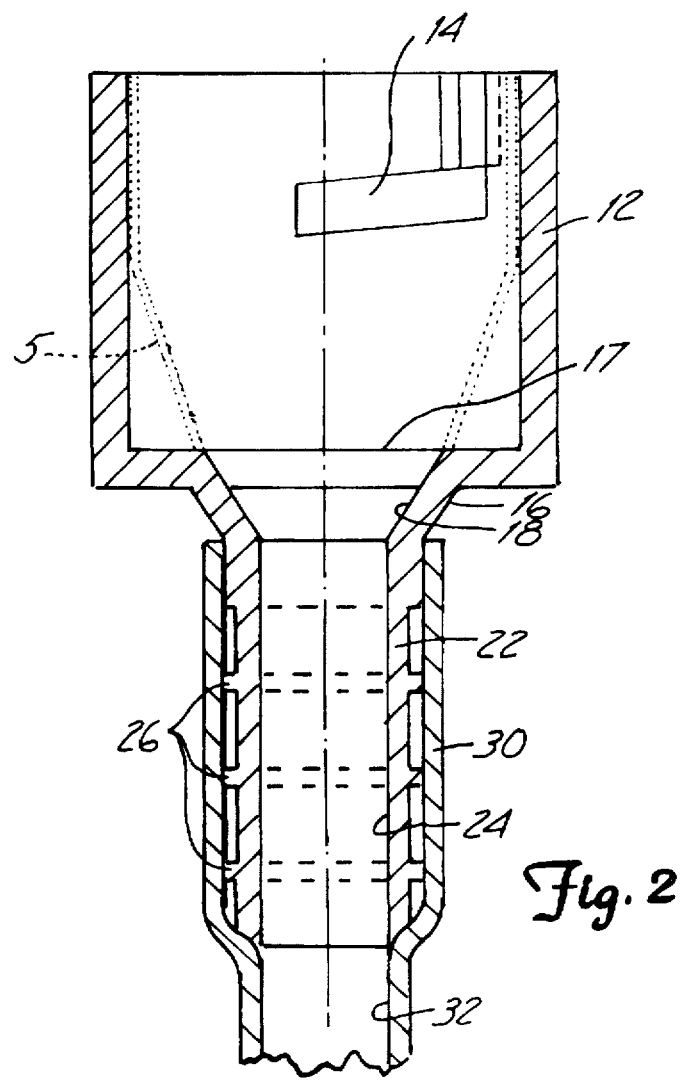
FIG. 2 shows a side view of the application system according to FIG. 1 in cross-section.

The application system according to FIGS. 1 and 2 is provided with a cap 10, whose cylinder-shaped upper part 12 is adapted to the receptacle out of which the plastic materials are to be applied and accommodates the front part of the receptacle up to its outlet. The receptacle which is provided with one or more pegs at its outer circumference can be connected with the cap 10 by means of a bayonet catch 14 with which the pegs engage, wherein the relative radial position of the receptacle and the cap can be reproducibly adjusted. The wall of the introduced receptacle 5 is indicated in FIG. 2 by the dotted lines. The axis of the receptacle and the application system is designated by reference sign 6.

The cap of the application system is furthermore provided with an outlet piece 16 having a funnel-shaped part. The upper opening 17 of the funnel-shaped part is transverse or elongate and corresponds in its shape to the outlet of the receptacle. If assembled, the opening 17 is essentially in the same plane as the outlet of the receptacle. The inner surface 18 of the funnel part tapers from the opening 17 downwards such that the lower cross-section 19 of the funnel is rotationally symmetrical or round. As indicated by the broken line 20, the outer surface of the funnel part is rotationally symmetrical.

The funnel-shaped part of the outlet 16 of the cap 10 passes into a cylindrical part 22 whose inner cross-section 24 or whose inner surface corresponds to the cross-section 19. The transition between the funnel-shaped part and the cylindrical part 22 can be rounded for reasons of fluid mechanics. Three ring profiles 26 having undercuts are provided at the outer circumference of the cylindrical part 22. A tube 30 is mounted over the cylindrical part 22, which is preferably slipped over the cylindrical part 22 after being heated and held by means of the undercut ring profiles 26. The tube 30 serves; as the elongate application part. The inner cross-section 32 or the inner surface of the non-expanded tube corresponds to the inner cross-section 24 or the inner surface of the cylindrical part 22 and forms an elongation thereof without any shoulder. The tube may have, for instance, an inner cross-section of 6 to 10 mm and a wall thickness of 1 mm.

In the embodiment according to FIG. 3, reference signs identical to those in FIGS. 1 and 2 designate the same parts. In the embodiment according to FIG. 3, a thread 36 is provided at the outer circumference of the cylindrical part 22 of the cap 10, by means of which the application part is fixed and secured to the cap (outlet piece). The thread 36 facilitates the mounting of the application part. In the embodiment according to FIGS. 3a and 3b, the application part is a foldable tube 40. In the lower part of FIG. 3a, the folding of the tube 40 is schematically shown. FIG. 3b shows a cross-section along the line A—A of FIG. 3a, in which the folding of the tube 40 is shown. During the application of the plastic mass, the tube 40 unfolds such that there is no shoulder at the transition between the application part or the cap 10 and the tube 40, and the plastic mass can thus flow in an unhindered manner.

By means of the above described embodiment according to FIGS. 2 and 3 it is guaranteed that no shoulder is formed either at the transition between the outlet of the receptacle and the mouth of the funnel part of the cap or at the transition between the outlet end of the cylindrical part of the cap and the inner surface of the tube, and thus an easy and complete application of the plastic mass without any losses is ensured.

What is claimed:

1. An application system for applying bone cement out of a receptacle into a medullary cavity, the application system comprising:

an outlet piece adapted to receive the receptacle, the outlet piece having a smooth inner surface and an outside; and an elongate application part attachable to the outside of the outlet piece, the application part having a longitudinally extending space which mates with the outlet piece with no inner shoulder, the application part formed of a deformable, flexible material and having a plurality of longitudinally extending folds which freely fold, allowing the application part to be inserted into the medullary canal in a freely folded state and then deform and expand due to bone cement introduced into the longitudinally extending space.

2. The application system according to claim 1, wherein the outlet piece comprises a funnel-shaped part.

3. The application system according to claim 2, wherein the outlet piece comprises a rotationally non-symmetrical funnel.

4. The application system according to claim 1, which has a two-piece structure.

5. The application system according to claim 1, wherein the application part in its unfolded condition has a length of approximately 3 to 25 cm.

6. The application system according to claim 1, wherein outlet piece comprises a bayonet catch for receipt of the receptacle.

7. The application system according to claim 1, wherein the application part is mounted at least partially over the outside of the outlet piece, and wherein the outside of the outlet piece comprises at least one sharp-edged extension having an undercut for holding the application part.

8. The application system according to claim 1, wherein the longitudinally extending folds are located at a free end of the application part and extend for only a portion of the application part, and wherein the application part comprises a non-foldable attachment part for mating with and attaching to the outlet piece.

9. The application system according to claim 1, wherein the outlet piece is formed of a material selected from the group consisting of: TPX, rubber, silicon, polycarbonate, metal and glass.

10. The application system according to claim 1, wherein the application part is formed of a smooth elastic material.

11. The application system according to claim 10, wherein the application part is formed of TEFLON.

12. A method of applying bone cement out of a receptacle into a medullary cavity, the method comprising:

attaching an outlet piece to the receptacle, the outlet piece having a smooth inner surface and an outside; and attaching an elongate application part having a longitudinally extending space to the outside of the outlet piece such that the longitudinally extending space mates with the outlet piece with no inner shoulder, the application part formed of a deformable, flexible material and having a plurality of longitudinally extending folds which freely fold, allowing the application part to deform and expand due to bone cement introduced into the longitudinally extending space;

inserting the application part in a freely folded state into a medullary canal; and introducing bone cement through the outlet piece into the application part such that the bone cement deforms and expands the application pair such that the applied bone cement essentially completely fills the medullary cavity.

13. The method of claim 12 for applying PMMA bone cements.

14. The method of claim 12, further comprising the step of:

after filling the application part, retracting the application part longitudinally out of the medullary cavity while leaving the applied bone cement in position in the medullary cavity.

* * * * *

UNITED STATES PATENT AND TRADEMARK OFFICE
CERTIFICATE OF CORRECTION

PATENT NO. : 5,788,702
DATED : AUGUST 4, 1998
INVENTOR(S) : KLAUS DRAENERT

It is certified that error appears in the above-identified patent and that said Letters Patent is hereby corrected as shown below:

Col. 3, line 25, delete "serves;", insert --serves--

Col. 4, line 54, delete "pair", insert --part--

Signed and Sealed this

Twenty-first Day of September, 1999

Attest:

Q. TODD DICKINSON

*Attesting Officer*     *Acting Commissioner of Patents and Trademarks*